United States Patent [19]

McClure

[11] 4,208,541

[45] Jun. 17, 1980

[54] METHOD FOR THE REMOVAL OF CARBONYL SULFIDE FROM LIQUID PROPANE

[75] Inventor: George McClure, 2401 Seaboard, Midland, Tex. 79701

[73] Assignees: George McClure, Midland; David C. Morrow, Odessa, both of Tex.

[21] Appl. No.: 907,602

[22] Filed: May 19, 1978

Related U.S. Application Data

[63] Continuation-in-part of Ser. No. 749,464, Dec. 10, 1976, abandoned.

[51] Int. Cl.² ............................................... C07C 7/00
[52] U.S. Cl. .................................................... 585/860
[58] Field of Search ........ 260/676 AD, 676 H, 676 R; 423/228, 243, 416; 585/860

[56] References Cited

U.S. PATENT DOCUMENTS

| | | | |
|---|---|---|---|
| 2,309,871 | 2/1943 | Schulee et al. | 260/676 AD |
| 2,712,978 | 7/1955 | Blohm et al. | 423/228 |

OTHER PUBLICATIONS

W. W. Williams, "Treatment of Gas Plant Liquids With Diglycolamine Agent", paper prepared for presentation at the Oklahoma Regional Meeting of the Natural Gas Producers Association, Oklahoma City, Ok. (Apr. 12, 1973).

*Primary Examiner*—Delbert E. Gantz
*Assistant Examiner*—Wayne A. Langel
*Attorney, Agent, or Firm*—Arnold, White & Durkee

[57] ABSTRACT

A method for the removal of carbonyl sulfide from liquid propane under liquid-liquid contact conditions by mixing liquid propane containing carbonyl sulfide as an impurity with 2-(2-aminoethoxy) ethanol as the principal agent for the carbonyl sulfide removal. The 2(2-aminoethoxy) ethanol is reclaimed and reused for further carbonyl sulfide removal.

5 Claims, 1 Drawing Figure

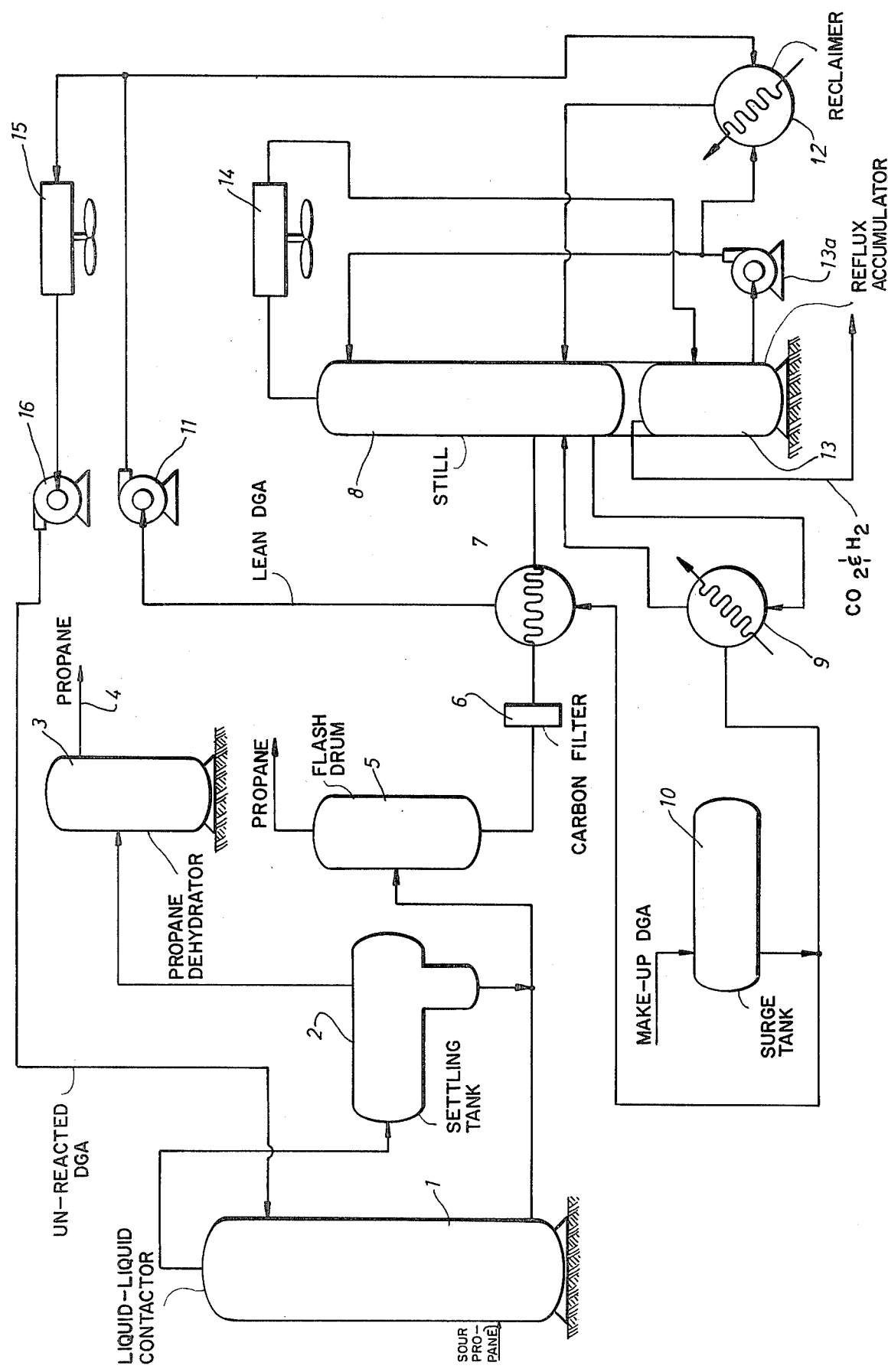

METHOD FOR THE REMOVAL OF CARBONYL SULFIDE FROM LIQUID PROPANE

RELATED APPLICATION

This application is a continuation-in-part of application Ser. No. 749,464, filed Dec. 10, 1976, now abandoned.

BACKGROUND OF THE INVENTION

1. Field of the Invention

This invention relates to the removal of carbonyl sulfide from liquid propane utilizing as the principal agent 2-(2-aminoethoxy) ethanol.

2. Description of the Prior Art

Treatment of gasoline plant, refinery, or other processing plant liquid products for removal or conversion of undesirable components including sulfur compounds is a complex and costly necessity for the petroleum fuel processing industry. Such undesirable compounds include, for example, hydrogen sulfide, mercaptans, sulfides and carbonyl sulfide as well as carbon dioxide.

Methods existing prior to the invention described herein for the removal of carbonyl sulfide from natural petroleum fuels have quite often been performed on fuels in a gaseous state. For example, widely relied upon procedures in the natural gas industry for removing sulfide impurities from gaseous state fuels have utilized monoethanolamine (MEA), diethanolamine (DEA), tetraethyleneglycol (TETRA), or diisopropyl amine (DIPA).

It is also well established in the literature that 2-(2-aminoethoxy) ethanol, also known by the trademarked name DIGLYCOLAMINE®, and hereinafter often referred to as DGA, has been used either by itself or in combination with other materials to remove sulfide components from gaseous streams of petroleum fuels and petroleum derived products. Thus, the manufacturer of DGA has stated in a technical bulletin that "the major use of DIGLYCOLAMINE® brand of 2-(2-aminoethoxy) ethanol is for the removal of hydrogen sulfide ($H_2S$) and/or carbon dioxide ($CO_2$) from gas streams." Jefferson Chemical Company, Inc., Technical Bulletin, DIGLYCOLAMINE®, Jefferson Chemical Company, Inc., 3336 Richmond Ave., Box 53300, Houston, Tex. 77052.

The use of DGA for removing acid gases from a gaseous mixture stream of wet or dry hydrocarbons is the subject of U.S. Pat. No. 3,712,978 (July 12, 1955) and of Canadian Pat. No. 505,164 (Aug. 15, 1954), assigned to the Fluor Corporation, Ltd., Los Angeles, Cal. This is also described in an article entitled "Acid Gas Removal from Natural Gas Using Diglycolamine" by Howard L. Holder, presented at 45th Annual Convention of The Natural Gas Processors Association.

Additionally, it has been reported that MEA and DGA are substantially equivalent in their effectiveness for removing carbonyl sulfide from gaseous systems. Dingman & Moore, *Compare DGA and MEA Sweeting Methods,* Hydrocarbon Processing, Vol. 47, No. 7, July, 1968.

Jones and Payne have reported success in using a DGA-water mixture as a solvent in an aromatic extraction treatment of hydrogenated pyrolysis gasoline. They have reported that the DGA-water solvent is more effective for removing benzene-toluene and toluene-xylene mixtures from gasoline than other currently used solvents such as TETRA or DEG-DPG mixtures. Jones and Payne, *New Solvent to Extract Aromatics,* Hydrocarbon Processing, March, 1973, 91–92.

The Naval Research Laboratory has compared the use of DGA with MEA, N,N' dimethylacetamide (DMAC), and tetramethylene sulfone (TMS) as regenerative carbon dioxide absorbants. It was reported that TMS was superior to the other solvents when employed in $CO_2$ scrubbers on nuclear submarines. Gustafson and Miller, *Investigation of Some New Amines as Regenerative Carbon Dioxide Adsorbants,* Naval Research Laboratory, NRL Report 6926, July 23, 1969.

DGA has been used by the El Paso Natural Gas Company for the removal of acid gas impurities from gas streams containing 2% or more of total acid gas. In side-by-side comparisons of a mixture of MEA-DEG solvents with DGA, it was found that DGA was capable of producing approximately a 50% saving in capital investment because the more efficient DGA solvent characteristics resulted in reductions of solution pumping horsepower, reboiler drive steam, cooling tower loads, etc. H. L. Holder, *Diglycolamine-A Promising New Acid-Gas Remover,* The Oil & Gas Journal, May 2, 1966, 83–86.

The need for complete carbonyl sulfide removal from liquid propane is quite apparent when one considers that hydrolysis of carbonyl sulfide results in the production of carbon dioxide and hydrogen sulfide. The reaction becomes distressingly apparent in petroleum treatment systems which incorporate catalytic dehydrators used to dry purified petroleum products. For example, it was reported in 1962 that propane dehydrators used in a Mobil Oil Company underground storage facility started producing hydrogen sulfide in the effluent stream. Investigations established that the inlet stream of gaseous propane contained trace quantities of carbonyl sulfide. Apparently, activated alumina used in the propane dehydrators catalyzed the hydrolysis of carbonyl sulfide and resulted in hydrogen sulfide contaminated effluent. The problem was solved by Mobil Oil Company not by using a solvent to remove the carbonyl sulfide from the inlet propane stream, but by utilizing a silica-alumina absorbant which had been specially treated to prevent the catalyzed hydrolysis. Fairs and Rumbaugh, *Carbonyl Sulfide Hydrolyses in Propane Dehydrator,* Hydrocarbon Processes and Petroleum REFINER, 41(11), November, 1962, 211.

Shell Oil Company has suggested a method for the removal of carbonyl sulfide and hydrogen sulfide from liquid propane. This process is known as the ADIP process and is based upon an absorption-regeneration cycle using a circulating aqueous solution of an alkanolamine such as diisopropyl amine. Shell Oil indicates that liquid propane treated by the ADIP process results in a carbonyl sulfide content in liquid propane after the treatment of less than 2 ppm by weight. Shell Oil Company, *ADIP,* Hydrocarbon Processing, April, 1975, 84.

British Pat. No. 1,513,786 (May 29, 1969) assigned to Shell International Research MAATSCHAPPIJ N.V., teaches the separation of acid gases such as carbonyl sulfide and hydrogen sulfide from gaseous mixtures by means of a selective absorbant of the general formula:

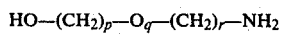

wherein p, q and r are integers, and p=2 to 3, q=1 to 4 and r=2 to 3

Signal Oil Company has reported on the treatment of gas plant liquids with DGA. Williams, W. W., *Treatment of Gas Plant Liquids with Diglycolamine Agent*, paper prepared for presentation at Oklahoma Regional Meeting of the Natural Gas Processors Association, Oklahoma City, Okla., Apr. 12, 1973. In that paper, it was reported that a liquid product mixture was treated with DGA prior to fractionation with the intent of minimizing or possibly eliminating the downstream sweetening processes. Initially, an MEA liquid-liquid contact system was constructed. This was subsequently converted to DGA in order to evaluate mercaptan removal with the added advantage that any carbonyl sulfide reaction with DGA produced regenerable degradation products. Table IV of this report, reproduced in part as Table 1 for convenience below, indicates that the raw product sought to be purified was a complex mixture of straight chain hydrocarbons with only approximately 48% of the mixture consisting of liquid propane. Results of chemical analysis after treatment with DGA, also found in Table IV of this report and reproduced in part below, show that only approximately 25% of the carbonyl sulfide found in the untreated raw product was removed after treatment with DGA, whereas significantly higher percentages of the hydrogen sulfide and mercaptan impurities were removed.

Regarding the foregoing, it becomes exceedingly apparent that the prior art usage of DGA has been nearly universally limited to the removal of acid gases from gaseous hydrocarbon streams.

TABLE 1

| COMPONENT | UNTREATED RAW PRODUCT | DGA TREATED PRODUCT | % REMOVAL OF IMPURITY* |
|---|---|---|---|
| Carbon dioxide | 10 ppm | NIL | 100% |
| Hydrogen sulfide | 11 ppm | 5 ppm | 54.5% |
| Carbonyl sulfide | 12 ppm | 9 ppm | 25% |
| Sulfur dioxide | 5 ppm | 7 ppm | |
| Carbon disulfide | NIL | 1 ppm | |
| Methyl mercaptan | 27 ppm | 20 ppm | 25.9% |
| Ethyl mercaptan | 32 ppm | 29 ppm | 9.5% |
| Propyl mercaptan +disulfides | 25 ppm | 13 ppm | 48% |
| Total mercaptans | 91 ppm | 66 ppm | 27.5% |
| Total sulfur | 122 ppm | 86 ppm | 29.5% |

Raw Product Stream Analysis Reproduced from Table IV of Williams, W. W., Treatment of Gas Plant Liquids with Diglycolamine Agent, paper prepared for presentation at Oklahoma Regional Meeting of the Natural Gas Producers Association, Oklahoma City, Oklahoma, April 12, 1973.
*This portion of the table was not presented in the original.

The one exception of this use has been the Signal Oil Company treatment of liquid hydrocarbon mixtures with DGA to remove impurities. However, even in this example the effectiveness of removal of carbonyl sulfide from the liquid mixtures has been minimal. Accordingly, prior to the development of the present invention, there has been no commercially acceptable, economically attractive method for substantially reducing the carbonyl sulfide content of liquid propane streams; therefore, the art has long sought a method which can effectively and economically reduce the carbonyl sulfide content absent the disadvantage of low percentage removal of carbonyl sulfide.

Applicant's application Ser. No. 749,464 filed Dec. 10, 1976 discloses an improved method for carbonyl sulfide removal from liquid propane, utilizing DGA as the principal agent in the carbonyl sulfide removal. This present application discloses and claims that same method, the mechanism for carbonyl sulfide removal now being more fully understood and described.

SUMMARY OF THE INVENTION

In accordance with this invention, the foregoing has been achieved through the present method for treating a hydrocarbon stream consisting essentially of liquid propane and containing carbonyl sulfide, and in particular, for the substantially 100% removal of carbonyl sulfide from such liquid propane stream.

The invention is a method for the removal of carbonyl sulfide from liquid propane by mixing under liquid-liquid contact conditions liquid propane containing carbonyl sulfide as an impurity with DGA as the principal agent for carbonyl sulfide removal. The temperature and pressure under which such mixing occurs is such as to retain the liquid propane in the liquid state. After this mixing occurs, the mixture is separated into two components, one being liquid propane substantially free of carbonyl sulfide and the other comprising DGA and DGA degradation products, including $H_2S$ absorbed by the DGA.

It has now been determined that the principal mechanism of carbonyl sulfide removal using DGA in accordance with the present invention involves a reaction of DGA with carbonyl sulfide to yield the degradation product N,N' bis (hydroxyethoxyethyl) urea (known as BHEEU) according the following equation:

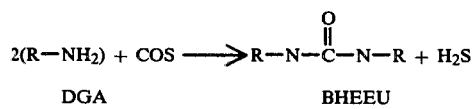

$$2(R-NH_2) + COS \longrightarrow R-N-\overset{\overset{O}{\|}}{C}-N-R + H_2S$$

DGA                          BHEEU where $R = HO-CH_2-CH_2-O-CH_2-CH_2$

As a result of this reaction the non-propane stream leaving the liquid-liquid contact apparatus will not show any appreciable carbonyl sulfide. Rather this stream will comprise any unreacted DGA, the BHEEU degradation product and hydrogen sulfide absorbed by the DGA. The expression "DGA and DGA degradation products" is therefore meant to embrace this stream which is formed by the reaction of DGA and carbonyl sulfide.

A further characteristic feature of this method is that the above reaction is reversible to the extent that the BHEEU can be reconverted to DGA in a suitable reclaimer, with the off gas of the reclaimer being essentially $CO_2$ DGA & $H_2O$. The DGA can then be used for further carbonyl sulfide removal, thereby making this method extremely commercially attractive.

BRIEF DESCRIPTION OF THE DRAWING

In the drawing, the single FIGURE illustrates a typical flow diagram for DGA removal from liquid propane in accordance with the present invention.

DESCRIPTION OF THE PREFERRED EMBODIMENT

The present invention embodies a method wherein carbonyl sulfide is removed from a liquid propane stream by utilizing certain characteristics of DGA. Sour liquid propane is flowed into intimate contact with DGA which acts to selectively remove the carbonyl sulfide from the liquid propane stream. As used herein, the expression "sour liquid propane" refers to liquid propane which has carbonyl sulfide impurities dissolved within it.

Referring now to the single FIGURE, at the outset of the purification process a stream of sour liquid propane is flowed into a liquid-liquid contactor 1 simultaneously with a stream of unreacted DGA, the flow rate of the DGA merely being such as to provide effective contact between the DGA and liquid propane. The selection of a particular flow rate can be easily carried out by one skilled in the art based on the nature of the liquid-liquid contactor, concentration of DGA, amount of carbonyl sulfide impurity, etc. As used herein, "un-reacted DGA" refers to the DGA prior to reaction with carbonyl sulfide or after regeneration from its degradation products. The unreacted DGA used in this method may be DGA itself, or aqueous solution of DGA. In operation of this method, regeneration of the DGA from BHEEU will not be totally complete. As a result the DGA used for the removal of carbonyl sulfide will generally contain some BHEEU. A typical system for use in this method will therefore comprise from about 5–90% by weight DGA, 10–40% by weight BHEEU and the remainder, if any, water. Aqueous solutions are preferred and it is preferred that the BHEEU concentration be in the range of 10–15% to reduce the viscosity of the treating liquid.

In the liquid-liquid contractor 1, the sour liquid propane stream may be flowed counter-currently to the unreacted DGA stream for the reason that adequate mixing is easily obtainable by such flow. The sour liquid propane stream may also be flowed co-current or cross-current to the unreacted DGA stream if provision is made for adequate mixing of the two liquids in the liquid-liquid contactor 1. The contact and/or mixing time for the liquids in the liquid-liquid contactor 1 is easily determinable through routine experimentation by one skilled in the art. Any commercially available liquid-liquid contactor system may be utilized, using for example, packed columns, bubble-type mixing or stratified plates.

The mixture resulting from this flow is thereafter separated into two components, the first containing DGA and DGA degradation products in water, and the second containing sweet liquid propane including a small amount of DGA soluble in liquid propane and water. As used herein "sweet liquid propane" refers to liquid propane which has been flowed into intimate contact with unreacted DGA, resulting in the removal of carbonyl sulfide from the sour liquid propane stream.

The second of these components is then flowed into a settling tank 2 wherein the DGA and water, both being heavier in weight than sweet liquid propane, migrate to the lower portion of the settling tank 2. Sweet liquid propane containing dissolved water is withdrawn and may be flowed into a propane dehydrator 3. Although not shown in the drawing, the sweet propane stream may be water washed before introduction into the propane dehydrator 3. The water wash system may include a suitable water separator for water removal. Activated alumina, bauxite, silicaalumina gel, molecular seives or similar materials may be present within the dehydrator 3 to act as a catalyst in the following reaction:

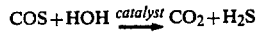

Thus, any carbonyl sulfide remaining in the water-saturated sweet propane reacts according to this above reaction with the hydrogen sulfide and any remaining unreacted carbonyl sulfide being adsorbed on the surface of the catalyst. After dehydration, the dehydrated liquid propane may be pumped via a line 4 to suitable facilities for storage or sale.

When the propane dehydrator 3 is utilized in the treatment process, it is preferred, for convenience only, that at least two dehydrator units, connected in parallel, be used. Thus, as one of the units is dehydrating the sweet liquid propane and simultaneously causing the above reaction to occur, the remaining unit or units undergo a regeneration cycle in which hot propane vapors may be passed over the surface of the catalyst, thus driving off any adsorbed water, hydrogen sulfide and carbonyl sulfide. These vapors may thereafter be condensed and recycled through the liquid-liquid contactor 1 where the hydrogen sulfide and carbonyl sulfide are removed.

Concurrently with the foregoing, the first stream removed from the liquid-liquid contactor 1 is flowed, preferably along with the DGA withdrawn from the settling tank 2, to a flash drum 5 in which any adsorbed propane is vaporized and removed. The rich DGA stream flows from the flash drum 5 to a carbon filter 6 wherein components such as heavy hydrocarbons and surfactants may be removed. The carbon filter 6 may be of any suitable type such as a model CF-120 made by the Perry Engineering Corporation.

The rich DGA stream from the carbon filter then flows through the tube side of heat exchanger 7 and into still 8. The still bottoms may be flowed through a reboiler 9 in which approximately 20% of the liquid may be vaporized. The reboiler 9 may be of any suitable type including either a steam reboiler or a fired reboiler. Preferably, the steam reboiler is of a standard kettle type having a weir overflow. The vapors from reboiler 9 are flowed back into still 8. The liquid from the reboiler is flowed together with makeup DGA from surge tank 10 through the shell side of heat exchanger 7. The surge tank 10 provides a convenient means for the introduction of make-up DGA and also provides for the continuous flow of lean DGA should the liquid stream from reboiler 9 be interrupted for any reason.

After passing through the shell side of heat exchanger 7 the pressure of the lean DGA stream may be increased by booster pump 11. Approximately 10–40% of the lean DEA stream may be diverted to reclaimer 12. In reclaimer 12 the BHEEU is converted to DGA through the application of heat and the addition of water or steam according to the reaction:

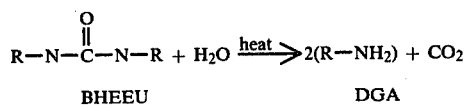

The lean DGA is preferably heated in reclaimer 12 to a temperature of from about 360° to about 400° F. to effect the DGA regeneration. The reclaimer 12 should preferably have a sparging line for the introduction of water from for example reflux accumulator 13, or for the introduction of steam for additional heating and mixing of the lean DGA stream. The vaporized stream from the reclaimer may then be flowed to still 8. It should be apparent that the flow of lean DGA into reclaimer 12 may be controlled by a suitable level controller.

The overhead from still 8 may be passed through a suitable condenser such as fan condenser 14 and may then be flowed to an overhead accumulator 13. The overhead gas from still 8 is generally comprised of $CO_2$ and $H_2S$. Water from the overhead accumulator may be recycled, via pump 13a, to still 8 and may be introduced into the reclaimer 12 through a sparging line.

It should be noted that still 8 and overhead accumulator 13 are shown in a stacked relationship and that this design has obvious advantages which are preferred.

For commercial application of this method, it is important that reclaimer 12 effectively regenerate DGA for reuse from its degradation product BHEEU. In addition to maintaining a sufficiently high temperature for thermal reversion, it is also preferred that reclaimer 12 be sized so as to accommodate the flow of liquid. As previously stated this flow should be approximately 10% to 40% of the total lean DGA flow rate.

The remainder of the lean DGA which is not passed through reclaimer 12 may be passed through a suitable cooler such as fan cooler 15. The lean DGA may then be pumped via pump 16 to the contactor 1.

Throughout the entire treatment process, the pressure and temperature of the system must be compatible to maintain the propane in the liquid state. Through experimentation, it has been established that the most effective treatment temperature range is between 60°–150° F. The pressure of the system is thereby correlated with this temperature range to assure the propane remains in the liquid state throughout the process.

The amount of DGA used in the practice of the present invention is variable depending on the carbonyl sulfide concentration existing in the sour liquid propane and is merely that amount of DGA effective to achieve the desired level of carbonyl sulfide removal. Such amount is easily determined by one skilled in the art through routine experimentation.

Typical liquid-liquid contactors, reclaimers, heat exchangers, other apparatus and the like, such as are commercially available, may be used to perform the invention disclosed herein. It should be understood that the method of the present invention is not be limited to the use of the apparatus as described above, and modifications within the foregoing description can be made while still falling within the spirit of the present invention. For example, it is possible to perform the present invention by simply mixing the unreacted DGA with sour liquid propane in a suitable mixing tank and thereafter separating, by specific gravity differences, the carbonyl sulfide-free liquid propane from the carbonyl sulfide containing DGA.

EXAMPLE

As an example of the effectiveness of the method disclosed herein, two series of experiments were run to determine the efficacy of DGA in the removal of carbonyl sulfide from a liquid propane stream. It should be understood that these procedures are provided simply to show the effectiveness of the present invention and in no way limit the scope of the invention or the procedures as described.

Procedure No. 1

In this series of experiments, 90% by weight liquid propane containing dissolved carbonyl sulfide impurity and 10% by weight of differing DGA concentrations are placed in a high pressure corrosion bomb. The bomb is then vibrated for five minutes to assure adequate mixing, and thereafter, the components are allowed to settle for fifteen minutes. Samples of the liquid propane are then drawn off and are subjected to gas chromatography analysis. Concentration of the DGA solution is varied from 0% DGA to 80% DGA in water. Table 2 lists the results of this experiment. Reference to Table 2 shows that there is a complete 100% removal of carbonyl sulfide from the liquid propane when the concentration of the DGA solution equals or exceeds 15%.

Procedure No. 2

Liquid propane is allowed to flash and is thereafter bubbled through 150 ml of the various aqueous DGA solutions which have previously been placed in 250 ml gas washing bottles. Vapors emanating from the washing bottles are sampled and injected directly into a gas chromatograph. Table 3 provides the results of this procedure. By referring to Table 3, one again sees that there is a complete 100% removal of carbonyl sulfide when the concentration of the DGA solution equals or exceeds 15%.

TABLE 2

| % DGA | Carbonyl Sulfide Remaining in Sample after Treatment, ppm | Grams Carbonyl Sulfide | % Carbonyl Sulfide Removed |
|---|---|---|---|
| 0 | 449 | 28 | 0 |
| 10 | 107 | 6 | 79 |
| 15 | 0 | 0 | 100 |
| 20 | 0 | 0 | 100 |
| 25 | 0 | 0 | 100 |
| 50 | 0 | 0 | 100 |
| 80 | 0 | 0 | 100 |

Results of carbonyl sulfide removal under Procedure No. 1

TABLE 3

| % DGA | Carbonyl Sulfide Remaining in Sample after Treatment, ppm | Grams Carbonyl Sulfide | % Carbonyl Sulfide Removed |
|---|---|---|---|
| 0 | 499 | 28 | 0 |
| 10 | 180 | 10 | 64 |
| 15 | 0 | 0 | 100 |
| 20 | 0 | 0 | 100 |
| 25 | 0 | 0 | 100 |
| 50 | 0 | 0 | 100 |
| 80 | 0 | 0 | 100 |

Results of carbonyl sulfide removal under Procedure No. 2

While the present invention has been described by reference to certain preferred embodiments and examples, it is to be understood that this invention cannot be limited thereto but rather must be construed as broadly as all or any equivalents thereof.

I claim:

1. A method for the removal of carbonyl sulfide from liquid propane, which comprises:
   mixing, under liquid-liquid contact conditions;
   (a) a stream of hydrocarbons consisting essentially of liquid propane containing carbonyl sulfide as an impurity; and
   (b) 2-(2-aminoethoxy) ethanol in an amount effective to remove substantially 100% of said carbonyl sulfide, at a temperature and pressure effective to retain said stream in the liquid state; and
   removing said stream from the system.

2. A method for the removal of carbonyl sulfide from liquid propane, which comprises:
   mixing, under liquid-liquid contact conditions;

(a) a stream of hydrocarbons consisting essentially of liquid propane containing carbonyl sulfide as an impurity; and (b) 2-(2-aminoethoxy) ethanol in an amount effective to remove substantially 100% of said carbonyl sulfide, at a temperature and pressure effective to retain said stream in the liquid state;

removing said stream from the system; and removing from the system the 2-(2-aminoethoxy) ethanol reacted with carbonyl sulfide.

3. A method for the removal of carbonyl sulfide from liquid propane which comprises:

(1) mixing, under liquid-liquid contact conditions,
  (a) a stream of hydrocarbons consisting essentially of liquid propane containing carbonyl sulfide as an impurity, and
  (b) unreacted 2-(2-aminoethoxy) ethanol, whereby said 2-(2-aminoethoxy) ethanol reacts with the carbonyl sulfide impurity to produce a degradation product of 2-(2-aminoethoxy) ethanol;

(2) separating the reaction mixture of step (1) into
  (i) a first stream of hydrocarbons consisting essentially of liquid propane substantially free of carbonyl sulfide impurity; and
  (ii) a second stream of 2-(2-aminoethoxy) ethanol and 2-(2-aminoethoxy) ethanol degration product;

(3) withdrawing said first stream (i) from the system;

(4) subjecting said second stream (ii) to thermal reversion to convert said 2-(2-aminoethoxy) ethanol degradation product to 2-(2-aminoethoxy) ethanol; and (5) returning the stream of 2-(2-aminoethoxy) ethanol formed in step (4) for further removal of carbonyl sulfide impurity from liquid propane.

4. The method of claim 3 wherein the liquid-liquid contact is carried out at a temperature of about 60° F. to 150° F.

5. The method of claim 3 wherein the thermal reversion is carried out at a temperature of about 360° F. to 400° F.

* * * * *